United States Patent [19]

Klausener et al.

[11] Patent Number: 5,449,806
[45] Date of Patent: Sep. 12, 1995

[54] PROCESS FOR THE PREPARATION OF DIALKYL CARBONATES

[75] Inventors: Alexander Klausener, Cologne; Heinz Landscheidt, Duisburg; Reinhard Langer, Krefeld; Paul Wagner, Düsseldorf, all of Germany

[73] Assignee: Bayer Aktiengesellschaft, Leverkusen, Germany

[21] Appl. No.: 272,497

[22] Filed: Jul. 8, 1994

[30] Foreign Application Priority Data

Jul. 15, 1993 [DE] Germany .................. 43 23 685.5

[51] Int. Cl.$^6$ .............................................. C07C 69/96
[52] U.S. Cl. ......................................................... 558/277
[58] Field of Search ............................................. 558/277

[56] References Cited

U.S. PATENT DOCUMENTS

| | | | |
|---|---|---|---|
| 4,732,918 | 3/1988 | Lohmueller et al. | 518/712 |
| 5,231,213 | 7/1993 | Landscheidt et al. | 558/277 |
| 5,235,087 | 8/1993 | Klausener et al. | 558/260 |
| 5,288,894 | 2/1994 | Landscheidt et al. | 558/277 |

FOREIGN PATENT DOCUMENTS

| | | |
|---|---|---|
| 425197 | 10/1990 | European Pat. Off. . |
| 464460 | 6/1991 | European Pat. Off. . |
| 503091 | 9/1991 | European Pat. Off. . |
| 501507 | 2/1992 | European Pat. Off. . |
| 503618 | 3/1992 | European Pat. Off. . |
| 523508 | 7/1992 | European Pat. Off. . |
| 523728 | 7/1992 | European Pat. Off. . |
| 538676 | 10/1992 | European Pat. Off. . |
| 3414717 | 10/1985 | Germany . |

OTHER PUBLICATIONS

"Palladium Supported Catalysts in CO+RONO Reactions"; Platinum Metals Rev. 1990, 34, 179.
Chinese Science Bulletin, vol. 34, No. 10, May 1989; pp. 875–876.
Translation from Rotha Fullford Leopold, Japanese Patent Spec. No. 60-181051 (1985).
Chemical Abstract, Synthetic High Polymers, vol. 104, 1986, p. 11.
"Fortschritte bei. der Modellierung von Festbettreaktoren", Chem.-Ing. Tech. 51, 1979, Mr. 4, pp. 257–265.

*Primary Examiner*—Robert W. Ramsuer
*Assistant Examiner*—Michael G. Ambrose
*Attorney, Agent, or Firm*—Sprung Horn Kramer & Woods

[57] ABSTRACT

Dialkyl carbonates can be prepared by reacting carbon monoxide with alkyl nitrites in a continuous gas phase reaction in the presence of a catalyst using a fixed bed reactor with a short catalyst bed in the direction of flow. The dialkyl carbonates are formed with almost quantitative selectivity; thermal decomposition of the alkyl nitrite, with the resulting formation of decomposition products, is not observed.

20 Claims, 9 Drawing Sheets

Fig. 18
Fig. 19
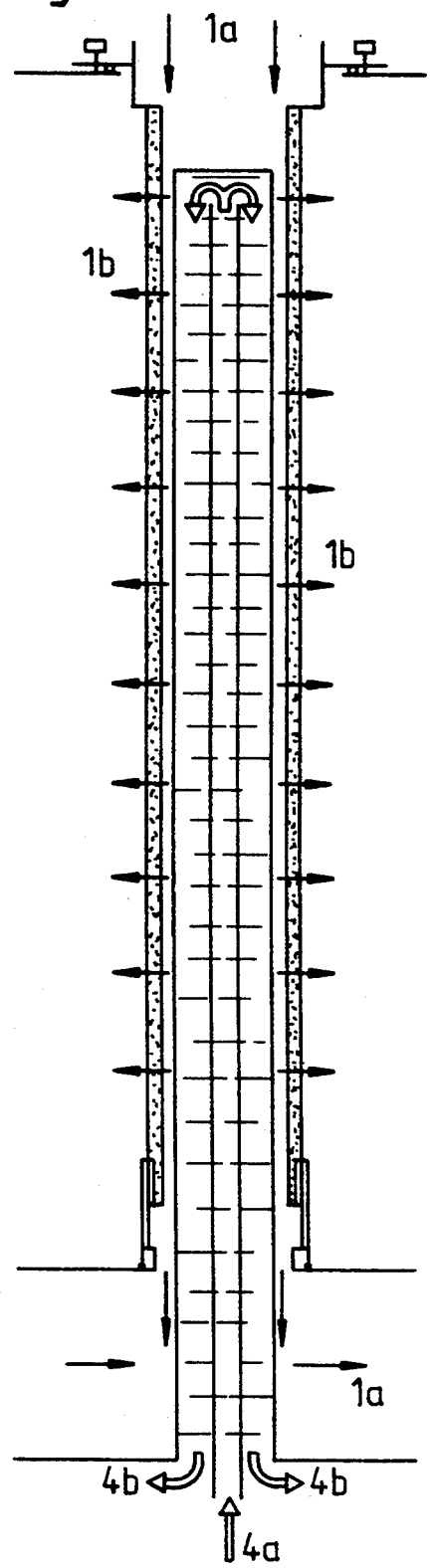
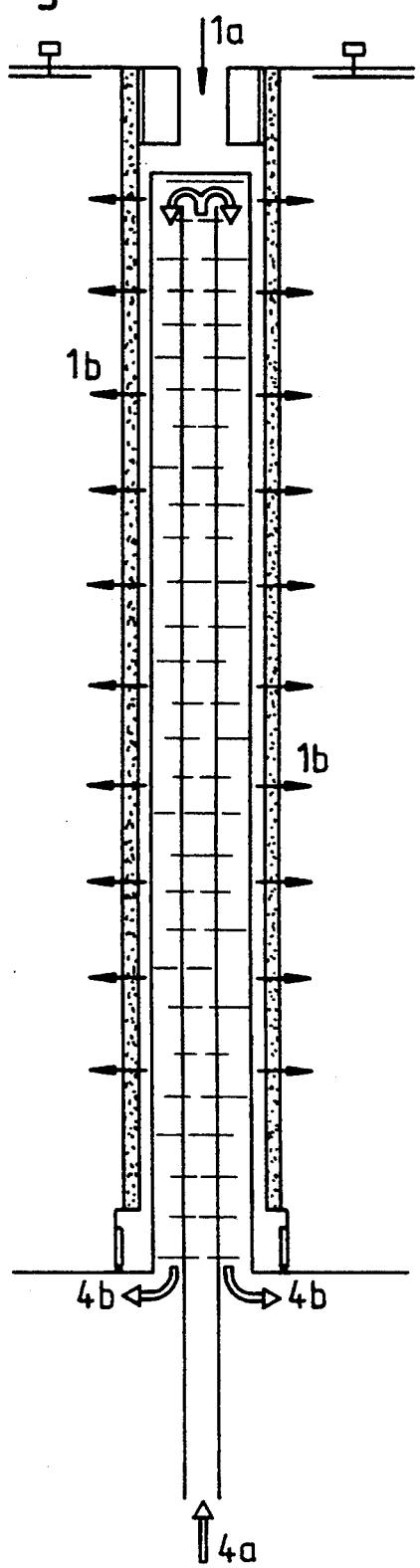

PROCESS FOR THE PREPARATION OF DIALKYL CARBONATES

BACKGROUND OF THE INVENTION

1. Field of the Invention

The present invention relates to a process for the preparation of dialkyl carbonates by reacting carbon monoxide with alkyl nitrites in the presence of a heterogeneous catalyst using a fixed bed reactor with a short catalyst bed in the direction of flow.

Dialkyl carbonates are of general chemical and industrial importance. Thus, for example, diethyl carbonate is an excellent solvent in the medium boiling range. Dialkyl carbonates are also excellent carbonylating and acylating reagents. They are of great importance in the preparation of other carbonates, urethanes and ureas. Finally, on account of their high oxygen content, they are suitable as fuel additives for improving the knock rating of motor fuels.

2. Description of the Related Art

It is known to prepare dialkyl carbonates by reacting phosgene or alkyl chloroformates with alcohols.

There is an increasing interest, however, in superseding the use of the toxic phosgene or the intermediates derived therefrom, such as chloroformic acid esters, by other processes.

Particularly important processes here are those in which carbon monoxide is reacted in the gas phase with alkyl nitrite on a platinum metal catalyst. This process is based on equation (1) (using dimethyl carbonate as an example).

(1) $CO + 2CH_3ONO \xrightarrow{[cat.]} H_3CO-CO-OCH_3 + 2NO$

Methyl nitrite itself can be produced for this purpose in a manner known per se, in an upstream reaction according to one of equations (2)–(5).

$4NO + O_2 + 4CH_3OH \rightarrow 4CH_3ONO + 2H_2O$ (2)

$NO + NO_2 + 2CH_3OH \rightarrow 2CH_3ONO + H_2O$ (3)

$N_2O_4 + CH_3OH \rightarrow CH_3ONO + HNO_3$ (4)

$2NaNO_2 + H_2SO_4 + 2CH_3OH \rightarrow 2CH_3ONO + Na_2SO_4 + 2H_2O$ (5)

The preparation of dimethyl carbonate by reacting carbon monoxide and methyl nitrite in the gas phase in the presence of a heterogeneous catalyst, preferably a supported catalyst containing a platinum metal, particularly preferably a supported catalyst containing palladium and very particularly preferably a supported catalyst containing a palladium halide, has been variously described, for example in the following scientific publications or patent publications:

JP 60/181 051; X.-Z. Jiang et al., Cuihua Xuebao 10(1), 75–78 (March 1989);

EP 425 197; X.-Z. Jiang, Platinum Metals Rev. 34(4), 178–180 (1990); EP 464 460; EP 503 091; EP 501 507; EP 503 618; EP 523 508; EP 523 728; EP 538 676.

One technical embodiment of this process is described in patent application EP 523 728. This Patent Application comprises the recycling of the nitrogen oxides released in the course of the reaction of methyl nitrite with carbon monoxide, together with the unreacted gaseous reactants and the additional gas required for rendering the system inert, preferably nitrogen, into a process step upstream of the actual dimethyl carbonate production process, which process step corresponds to equation (2) and in which the methyl nitrite required for the reaction is regenerated by feeding in methanol and oxygen and removing to the greatest possible extent the water released in this step. This is therefore a cyclic process in respect of the gaseous components involved, namely in respect of the inert gases and auxiliary substances, the unreacted gaseous reactants, for example the unreacted methyl nitrite and carbon monoxide, and the nitrogen oxides involved.

The actual process for the preparation of dimethyl carbonate for example, described by equation (1), takes place on a heterogeneous catalyst located inside a tube bundle reactor. A disadvantage here is the high thermal stress on the catalyst resulting from the substantial heat of the reaction between carbon monoxide and methyl nitrite which proceeds according to equation (1).

The thermally labile methyl nitrite is readily decomposed under these conditions.

It is therefore hardly surprising that 0.5 wt % of formaldehyde dimethylacetal, based on the dimethyl carbonate formed, is recovered in the crude product in the case of the procedure described in said Patent Application EP 523 728. For some intended applications of dimethyl carbonate, however, such impurities are unacceptable and extensive separation and purification steps are therefore necessary.

If such substances are low-boiling, as for example in the case of said formaldehyde dimethylacetal, further problems arise due to the inevitable accumulation of such volatile components within the whole of the basic cyclic process. To prevent the concentration of by-products within a process operated as an industrial cyclic process, specified proportions of the circulating gas and condensed reaction products, except for dimethyl carbonate itself, must be withdrawn continuously or batchwise, preferably continuously. This causes raw material losses and requires expensive off-gas treatments.

The object was therefore to carry out the reaction of the gaseous reactants carbon monoxide and alkyl nitrite on a heterogeneous catalyst in such a way that the heat of reaction thereby released is rapidly dissipated, thereby minimizing the formation of methyl nitrite decomposition products.

Continuous thermostatic control should be arranged for reactions with an extremely high heat tonality and catalysts or reactions with an extremely sensitive temperature behaviour.

Here the catalyst can be accommodated for example either between the tubes or else inside the tubes of a heat exchanger (a Linde reactor according to German Offenlegungsschrift 34 14 717 or a tube bundle reactor according to Chemie-Ingenieur-Technik 51 (1979), pp. 257–265).

Reactors of this type with tube diameters of one to several cm and tube lengths of 2–20 m have been state of the art for a long time.

Despite the constant flow of heat in the radial direction, a hot spot may be formed inside the reactor tubes, especially in larger reactors, for example in the synthesis of dimethyl carbonate from methyl nitrite, this being responsible for losses of selectivity as a result of the undesired formation of formaldehyde dimethylacetal.

SUMMARY OF THE INVENTION

Surprisingly, it has been found that the synthesis of dialkyl carbonate by the continuous reaction of carbon monoxide with alkyl nitrite on a heterogeneous catalyst containing one or more platinum metals, preferably containing palladium, in the gas phase, with continuous temperature control, can be effected without the formation of by-products by a process in which the catalyst bed takes the form of one or more flat layers of regular shape with a thickness of 0.01–50 cm, the surface of the catalyst layers being sealed by a gas-permeable layer, and this surface, on the educt feed side and/or on the product discharge side, facing a wall of similar regular shape, at a distance of 0.1–10 cm, which separates the space for the substances to be reacted from the space for the heat transfer medium, and the substances to be reacted being introduced in such a way as to flow through the catalyst bed perpendicularly to the flat catalyst layers.

BRIEF DESCRIPTION OF THE DRAWINGS

FIGS. 1, 2 and 4–19 show the basic design and basic mode of action of the reactors according to the invention and a few possible technical variants.

Figure 3:
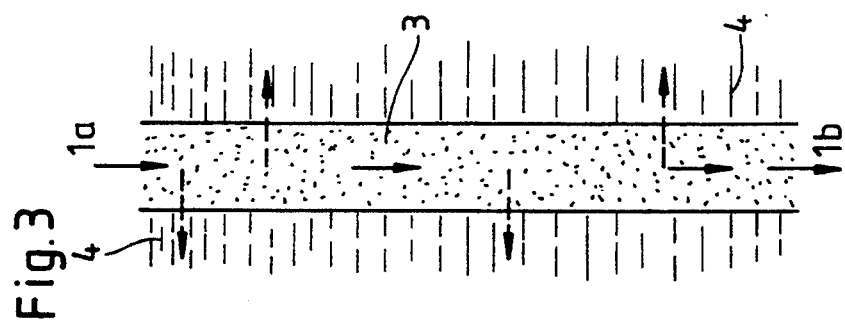
FIG. 3 shows a tubular reactor according to the state of the art.

In the attached drawings, the arrows with continuous shafts and reference numeral (1) denote the respective material flow from the educt feed (1a) (outlet substance/mixture of outlet substances, optionally together with a diluting gas or carrier gas) to the product discharge (1b) (reaction product/mixture of reaction products, optionally with diluting gas/carrier gas). The arrows with broken shafts and reference numeral (2) denote the heat flow from the catalyst to the heat transfer medium.

The dotted narrow areas (3) denote the catalyst bed sealed by a gas-permeable layer; the gas-permeable layer is not particularly highlighted in the drawings. The areas with horizontal broken lines (4) denote the space for the heat transfer medium, sealed by a wall.

DETAILED DESCRIPTION OF THE INVENTION

In a manner known to those skilled in the art, the heat transfer medium is to be regarded as moving through the reactor according to the invention and as being associated with external cooling for temperature control. Where the drawings are intended to show it by way of example, the flow of heat transfer medium is denoted by double-shafted arrows and reference numeral (4a) for the inlet and reference numeral (4b) for the outlet.

Figure 2:
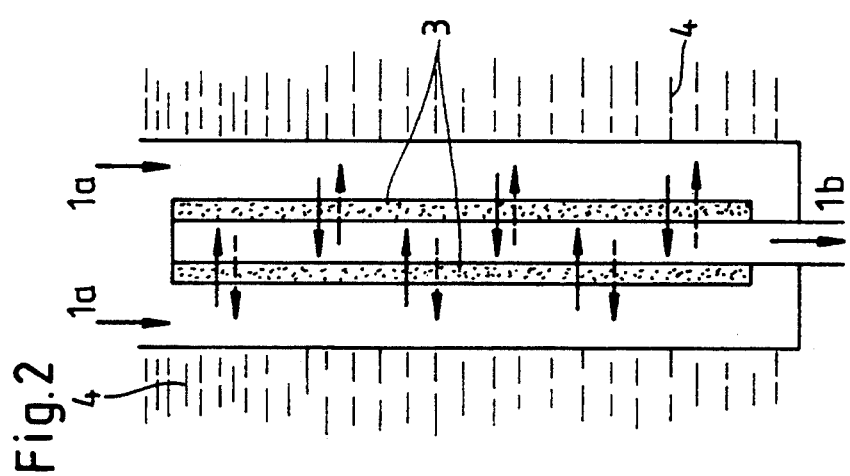
Figure 1:
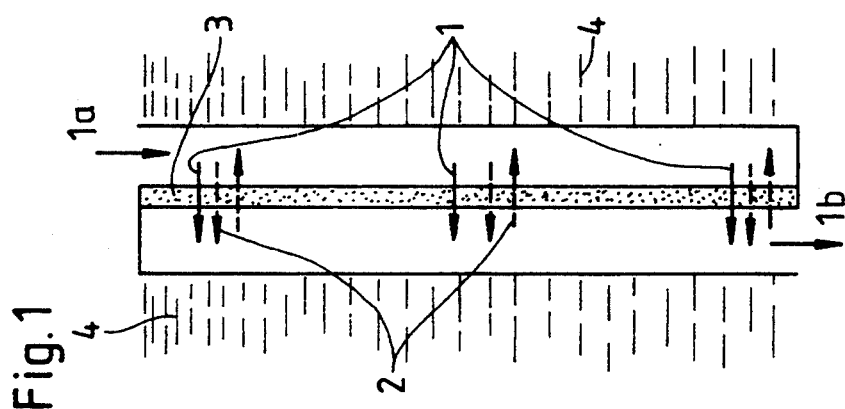
Figure 8:
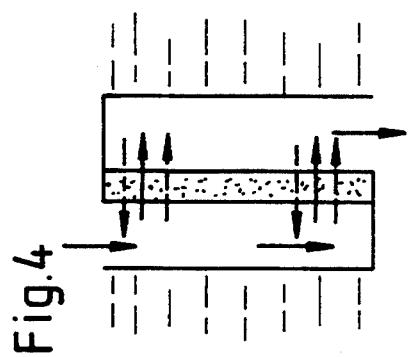
Figure 9:
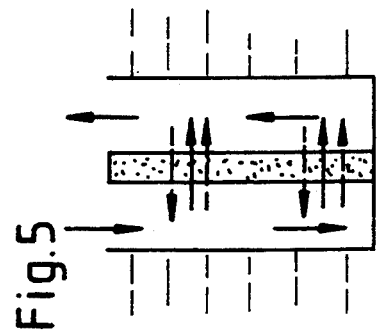
Figure 6:
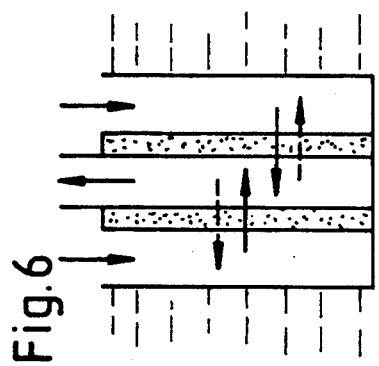
Figure 7:
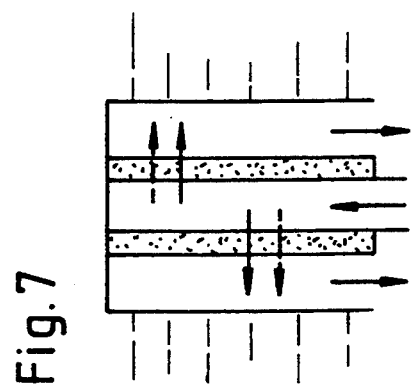

FIG. 1 shows the basic diagram of the reactor according to the invention in section through an even, flat catalyst bed with opposing spaces for heat transfer medium. FIG. 2 shows the basic diagram in section through a catalyst bed in the shape of a hollow cylinder. By contrast, FIG. 3 shows a tubular reactor according to the state of the art, again in section. Whereas, in the reactor according to the invention, the material and heat flows always run mutually parallel, antiparallel or both parallel and antiparallel, the material and heat flows in the conventional reactor are orthogonal to one another. Logically, the areas through which the material and heat flows pass are always identical in the reactor according to the invention, whereas they cannot be in the conventional reactor.

Figure 4:
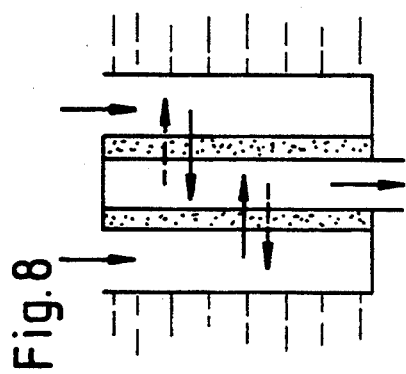
Figure 5:
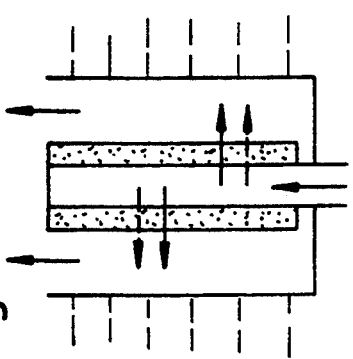

FIGS. 4–9 show variations of FIG. 1 and FIG. 2 where, in modified constructions—flat catalyst bed or hollow cylinder as catalyst bed, or feed and discharge of educt and product—the material and heat flows through the catalyst bed are parallel or antiparallel or both parallel and antiparallel. The heat flow is to be understood here are meaning the flow passing in the direction from the catalyst bed to the wall of the space for the heat transfer medium. For the sake of clarity, the additional numerical notation of the symbols has been left out in FIGS. 4–9. It can be seen that FIGS. 4 and 5 are related to FIG. 1 and FIGS. 6–9 are related to FIG. 2. In FIGS. 4 and 5, the heat flow moves both parallel and antiparallel to the material flow; in FIGS. 6–9, it moves either parallel or antiparallel.

Figure 10:
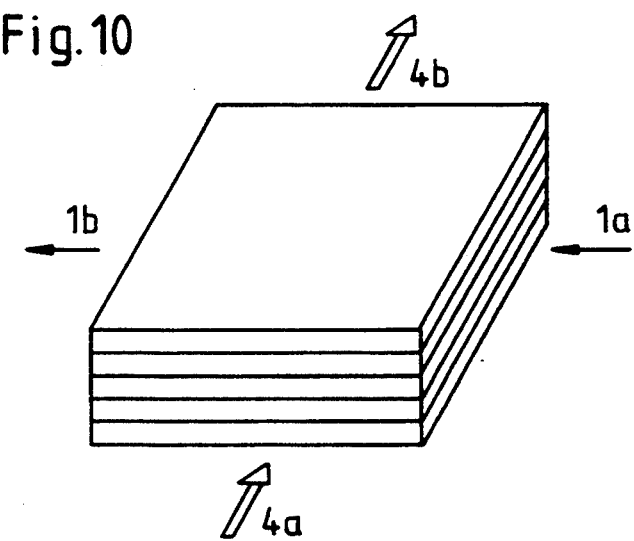
Figure 11A:
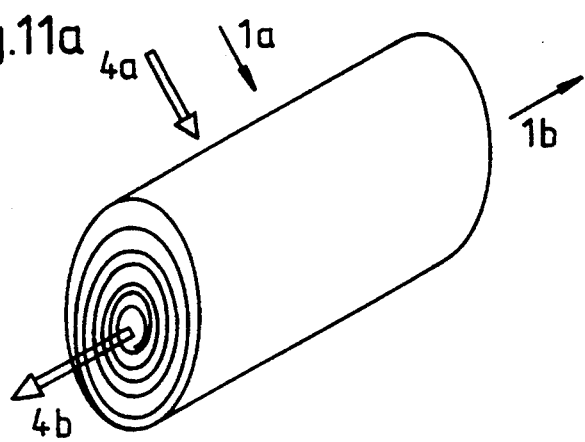
Figure 11B:
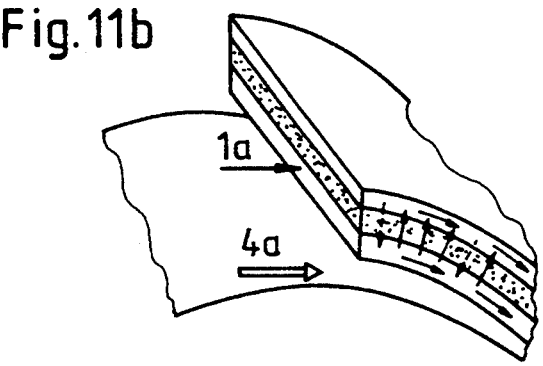
Figure 12:
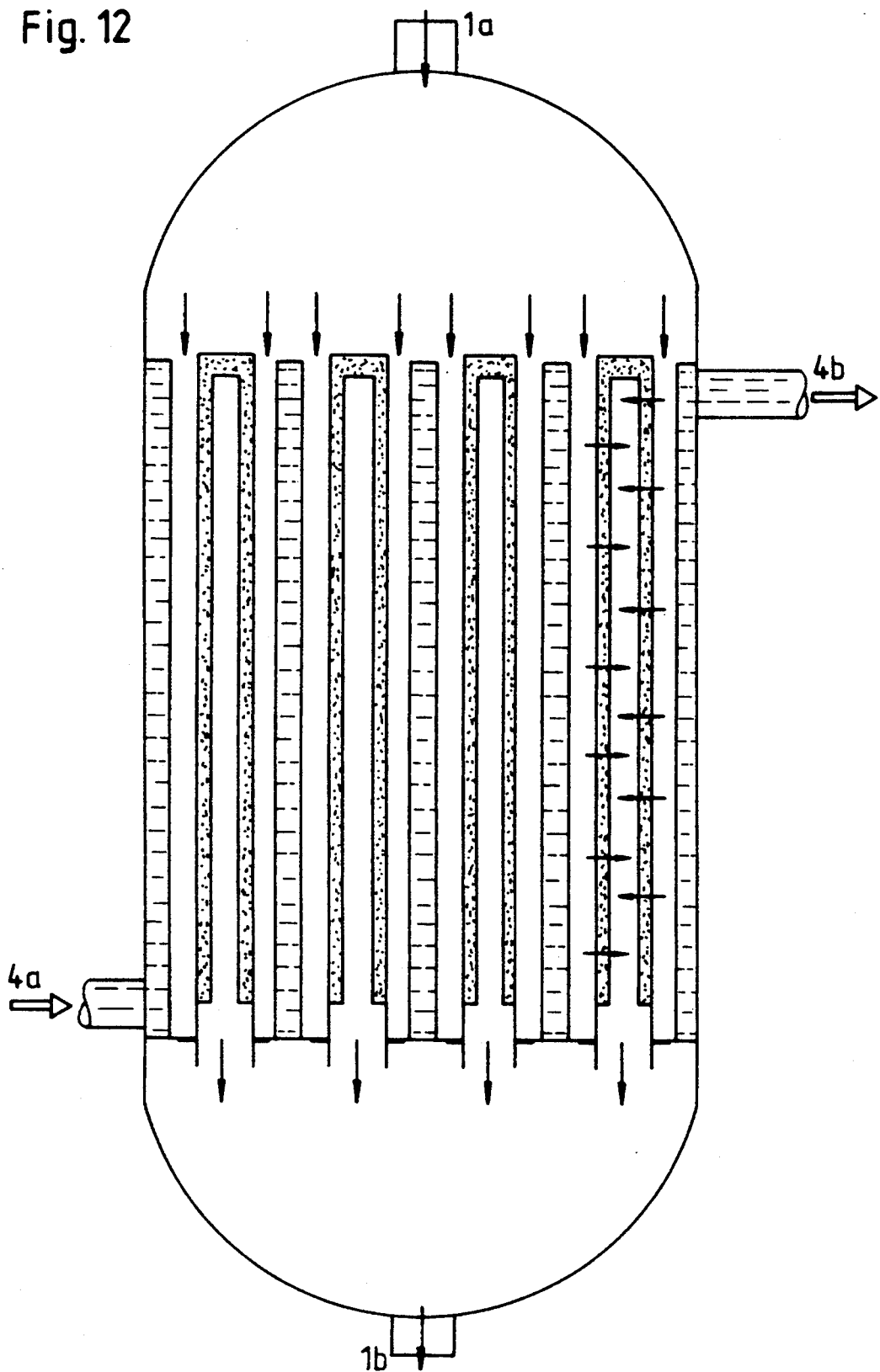
Figure 13:
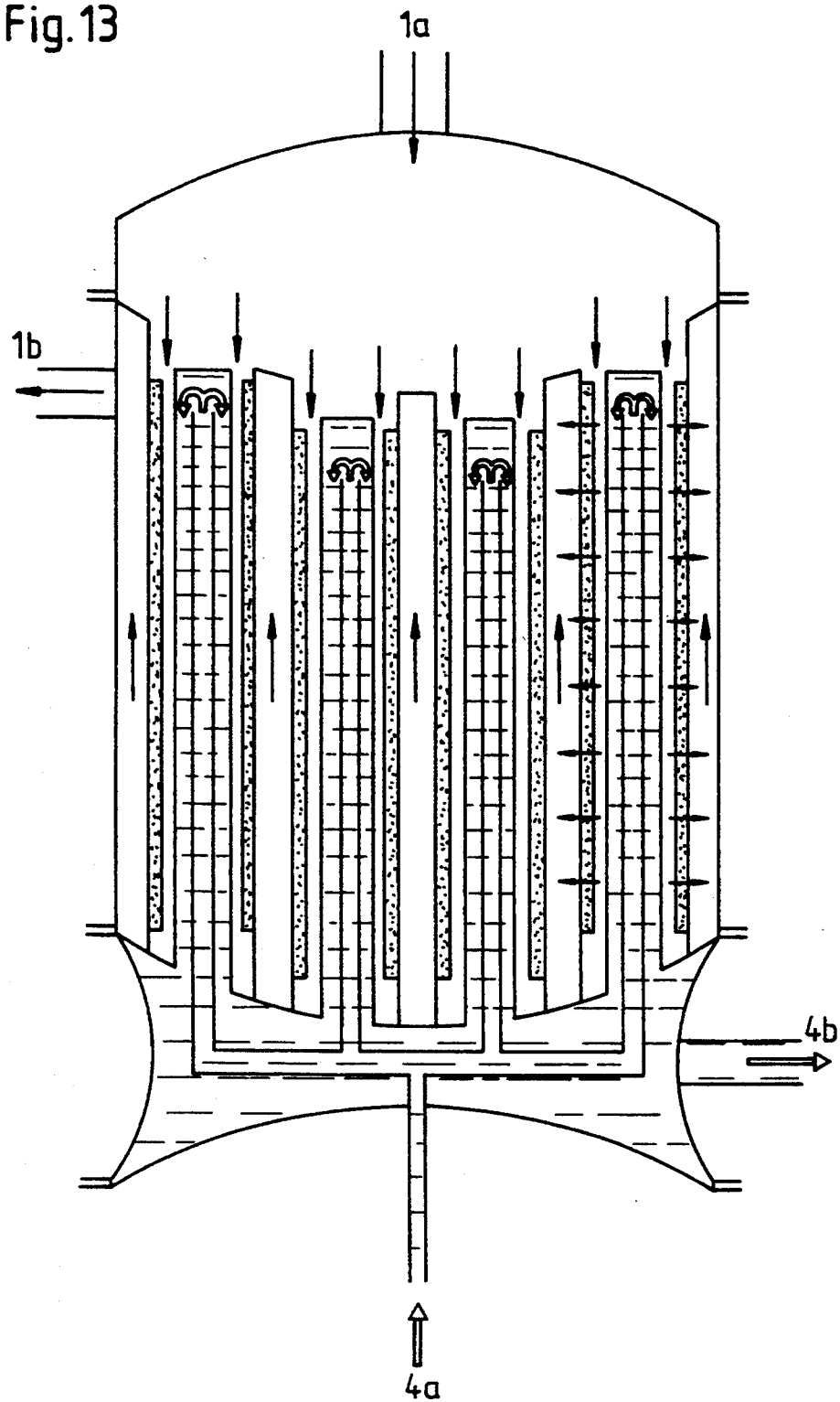
Figure 14:
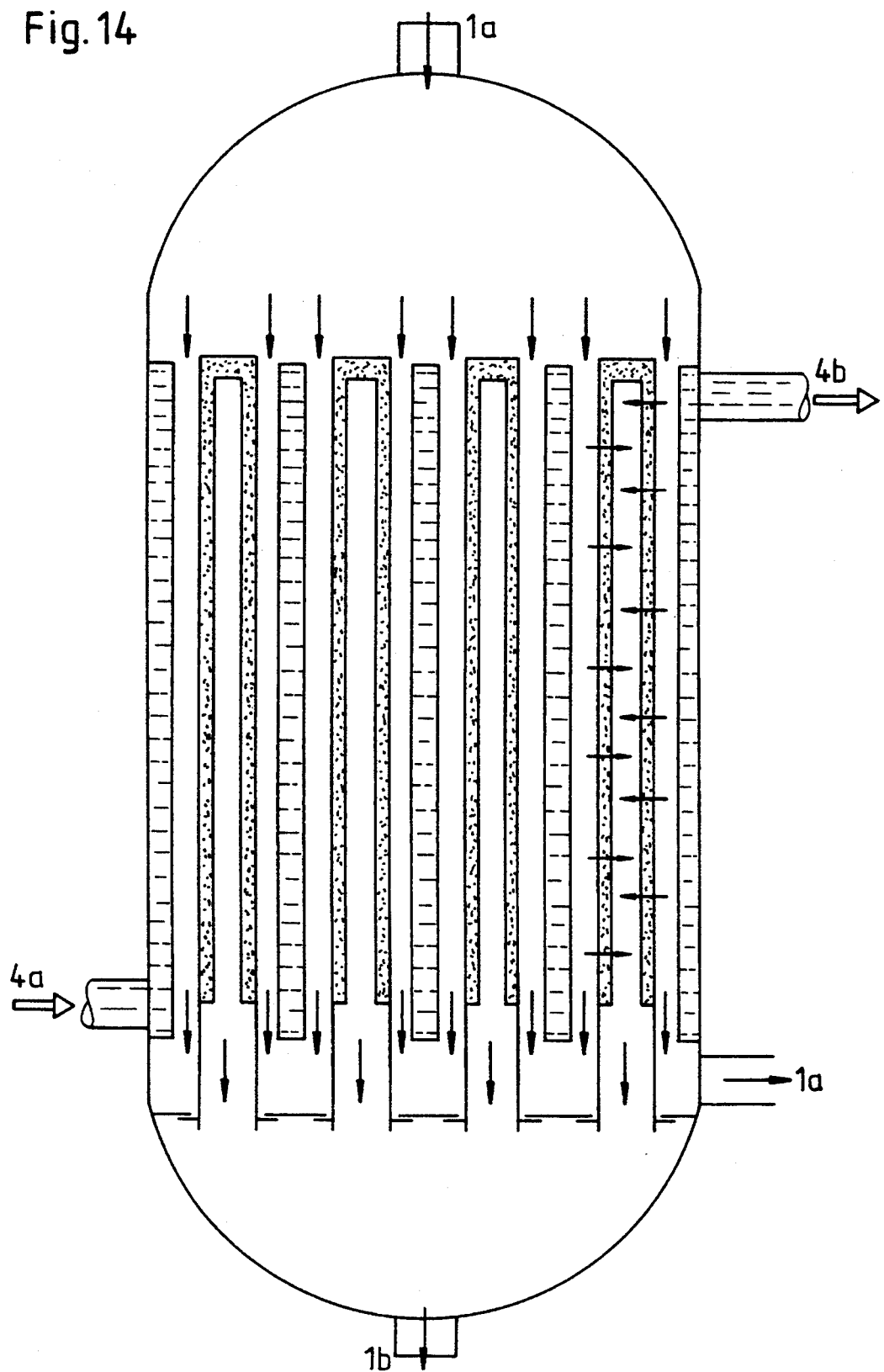
Figure 15:
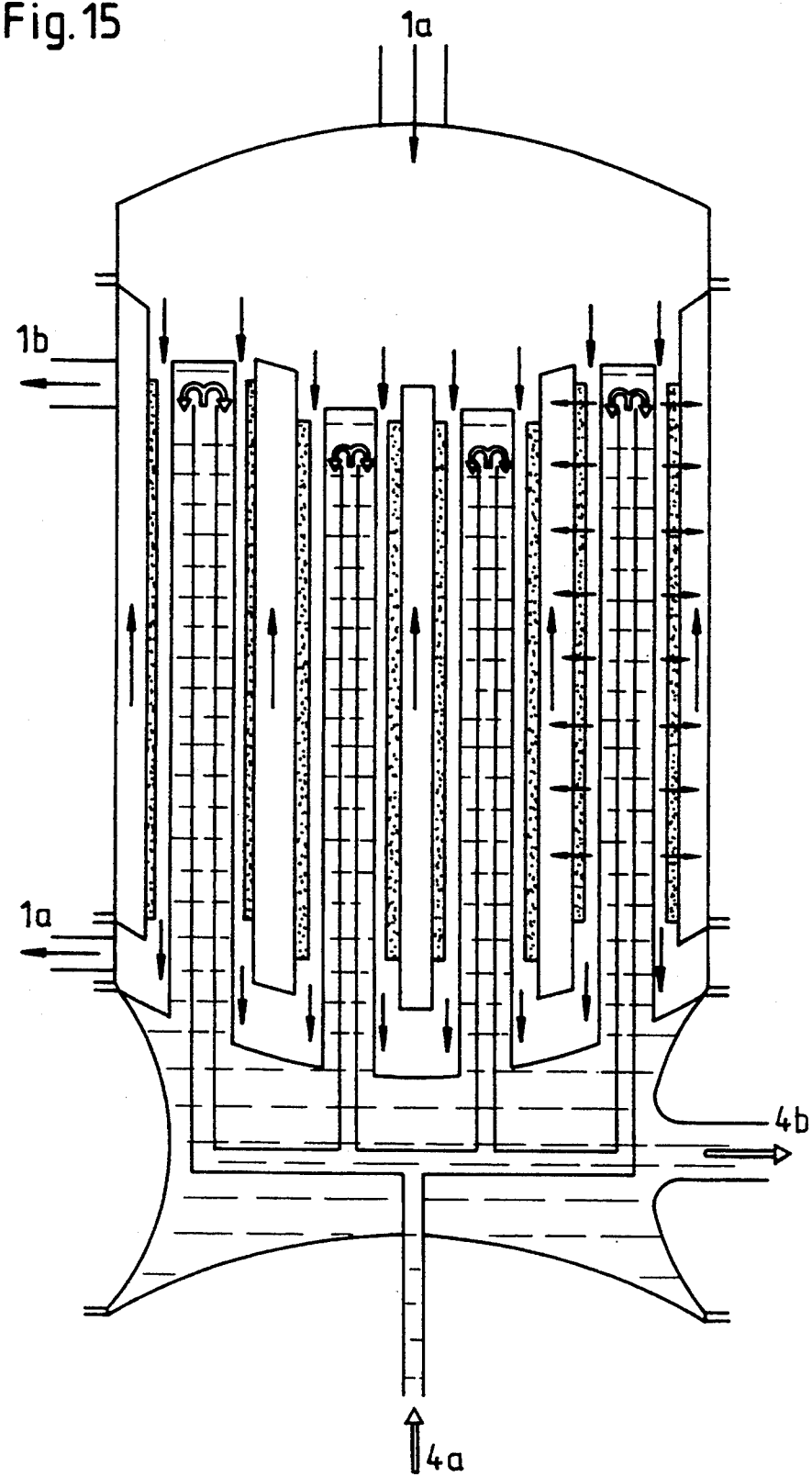
Figure 16:
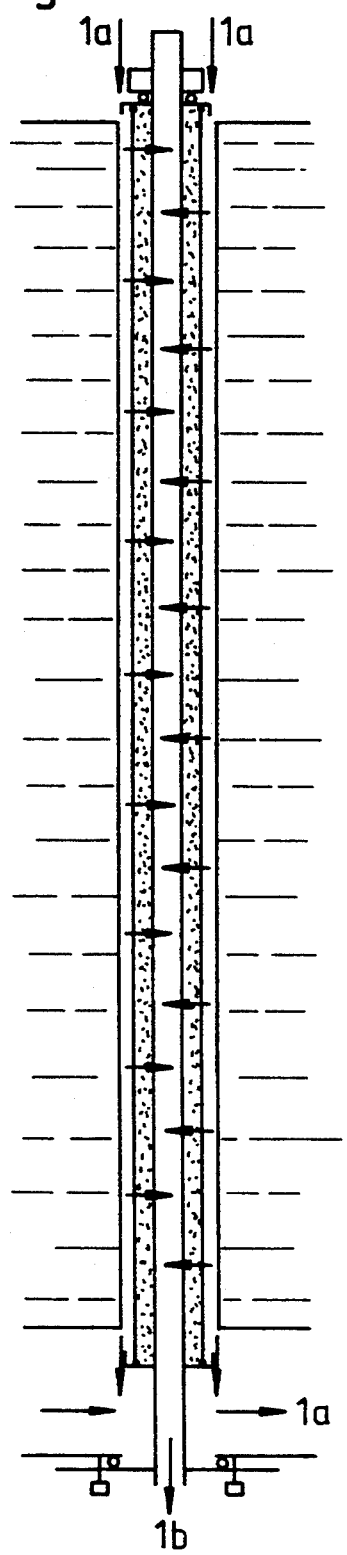
Figure 17:
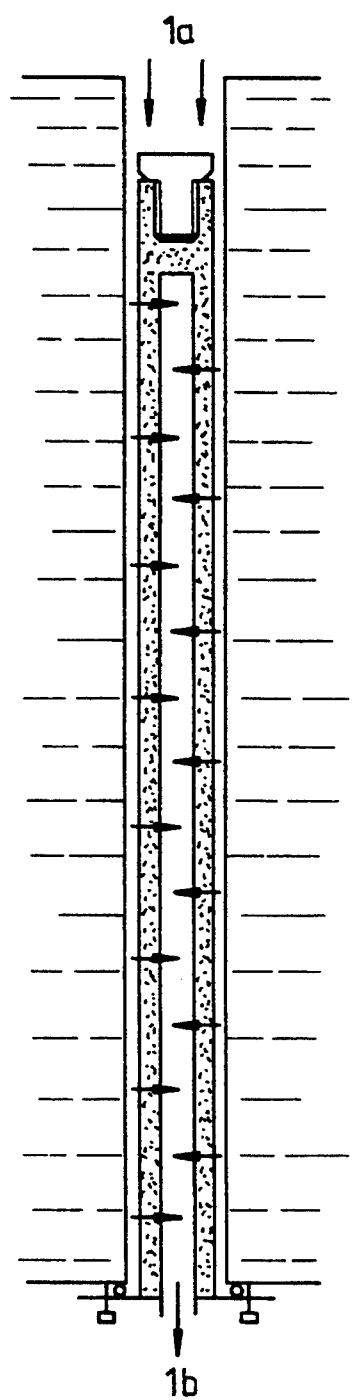

The catalyst bed can take the form of one or more flat layers. Thus the flat catalyst layers and the opposing walls of the spaces for the heat transfer medium, which are likewise of regular shape, can be combined in a stacked arrangement (cf. FIG. 10). However, the combination of flat catalyst and space for heat transfer medium can also be arranged in a "rolled-up" cylindrical form (cf. FIG. 11a). If, in the overall arrangement, the flows of material and heat transfer medium are also in mutually orthogonal directions, this does not apply specifically to the catalyst bed in the manner depicted above, as shown in FIG. 11b.

FIGS. 12–15 show possible technical embodiments using tube inserts in the manner of conventional tube bundle reactors. FIGS. 16–19 show individual tube inserts for such reactors, which can be screwed or welded into the reactor body or inserted in another way which is known in principle.

The reactors which can be used according to the invention are characterized in that the inflowing educt impinges on the largest possible catalyst surface and that at the same time the largest possible area is created for heat exchange. This means that, for a given space-time loading, there is a very low upflow loading and the catalyst is uniformly thermostated. This in turn means that, in the reactors according to the invention, as distinct from the known reactors with continuous thermostatic control, the heat flow is conveyed through the catalyst parallel or antiparallel or both parallel and antiparallel to the material flow. In this connection, the catalytically active beds in the reactors according to the invention have a particularly small dimension in the direction of flow. This dimension ranges from 0.01 to 50 cm, preferably from 0.02 to 20 cm, particularly preferably from 0.05 to 10 cm and very particularly preferably from 0.2 to 2 cm. The catalyst charge in the reactors according to the invention is retained by porous walls, which, in addition to fixing the catalyst charge, serve to guarantee a uniform flow through the catalyst bed over the entire surface. For this purpose, the flow resistance of these walls and of the catalyst bed must exceed a certain minimum value, which those skilled in the art can easily determine by experiment or calculation. In general, the minimum flow resistance of the catalyst beds, including the porous gas-distributing walls, should have values of 1 mbar to 10 bar, preferably of 2 mbar to 1 bar and particularly preferably of 5 mbar to 500 mbar.

The distance between the catalyst bed and the wall is 0.1 to 10 cm, preferably 0.2 to 8 cm, particularly preferably 0.3 to 6 cm and very particularly preferably 0.4 to 4 cm.

The porous walls in the reactors according to the invention are preferably made of sintered materials of appropriate porosity, such as that known to those skilled in the art of gas distribution. Sintered compacts made of metals are particularly preferred on account of their good thermal conductivity. Perforated screen constructions are also useful. They too must satisfy the conditions of distributing the educt gas stream over the catalyst without substantial local variations, and of guaranteeing a uniform flow through the charge; here again it is necessary to have a sufficient flow resistance, which can also be produced at least partially by the catalyst charge. For this purpose, the catalyst material must be sufficiently fine-grained adequately to guarantee the required pressure drop over the small penetration depth. It can also be seen that the catalyst must have a sufficient flowability to guarantee perfect packing during the filling process; thus, for example, the catalyst material must not have a tendency to stick. The relationship between particle shape and particle size, on the one hand, and the flow resistance of a charge of such particles, on the other, is known to those skilled in the art and can be determined by experiment.

The regularly shaped, flat layers of the catalyst bed are preferably hollow cylinders, sealed on one side, with diameters of 2 to 200 cm, for industrial-scale apparatuses preferably 7 to 100 cm and particularly preferably 10 to 50 cm; furthermore they are preferably arranged in the form of relatively large aggregates, e.g. as tube bundles.

Alkyl in educts and products has 1 to 4 carbon atoms and is for example methyl, ethyl, propyl, i-propyl, butyl or i-butyl, preferably methyl or ethyl and particularly preferably methyl.

Platinum metal catalysts contain one or more platinum group metals such as Pd, Ru, Rh, Pt or Ir, preferably Pd or Pd mixed with another platinum metal, and particularly preferably Pd by itself. The platinum metal is in the form of a salt, preferably a halide; it can also be in the form of a complex, e.g. $Li_2PdCl_4$. Examples of supports are charcoal, $Al_2O_3$ (e.g. $\gamma$-$Al_2O_3$), $SiO_2$, aluminosilicates, zeolites and other supports familiar to those skilled in the art.

The process according to the invention is carried out at a pressure of 0.1 to 10 bar and a catalyst temperature of 50° to 150° C.; the temperature is continuously maintained or controlled by a heat transfer medium.

The molar ratio alkyl nitrite:CO is 0.1–10:1, preferably 0.2–4:1 and particularly preferably 0.3–3:1. In known manner, an inert gas and/or the corresponding $C_1$-$C_4$-alkanol is added to the reactants.

EXAMPLE a) Preparation of the catalyst 10 ml of $\gamma$-aluminium oxide pellets of diameter 2–3 mm were impregnated with a solution of lithium tetrachloropalladate in water and dried at 60°–80° C. under vacuum. The catalyst then contained 8 g/l of palladium.

b) Description of the process

The reactor consisted of an oil-thermostated glass tube (length 62.0 cm, internal diameter 4.9 cm). A tube made of sintered glass material was arranged concentrically inside the thermostated glass tube. The sintered glass tube (length 15.0 cm, diameter 2.0 cm, porosity 3) was sealed off at the top end and sealed at the bottom end to an evacuated jacketed glass tube with a conical ground-glass joint (NS29 standard ground-glass joint) (diameter of inner glass tube 2.4 cm, diameter of outer glass tube 3.8 cm); the space between the inner and outer glass tubes was evacuated. The product gas was discharged through the inner glass tube. The outer glass tube had a length of 25.0 cm, measured from the NS29 conical ground-glass joint to the bottom end of the thermostated glass tube. At the end of the thermostated glass tube, the outer glass tube formed a gastight seal with the thermostated glass tube. Arranged concentrically with the inner sintered glass tube, there was another sintered glass tube inside the oil-thermostated glass tube (length 15.0 cm, internal diameter 3.2 cm, wall thickness 2 mm, porosity 3). This sintered glass tube was sealed at the bottom end to a female NS29 ground-glass joint, which fitted onto the male ground-glass joint of the jacketed vacuum tube to form a gastight connection. The outer sintered glass tube was sealed at the top end to a 10.0 cm long glass tube with a female NS29 joint. A ca. 10.0 cm long, evacuated ground-glass stopper fitted into this female joint to form a gastight connection.

The catalyst charge was located between the outer and inner sintered glass tubes.

The oil jacket of the reactor was thermostated at 90° C. and a gas mixture composed of 55 vol % of nitrogen, 20 vol % of methyl nitrite, 20 vol % of carbon monoxide and 5 vol % of methanol was passed over the catalyst. 200 ppm (by volume) of HCl were added to the gas mixture. The gas flowing out of the reactor was cooled to 5° C. and the condensed phase obtained was examined by gas chromatography.

The uncondensed products were determined by IR spectroscopy and mass spectroscopy.

Neither dimethyl oxalate nor methyl formate or formaldehyde dimethylacetal could be detected analytically in the reaction product containing the dimethyl carbonate formed.

c) Comparative Example 10 ml of the catalyst of Example a) were introduced into a vertical tubular reactor (glass, length 50 cm, diameter 4 cm) packed with Raschig rings.

The glass tube was heated to 90° C. and a gas mixture of 55 vol % of nitrogen, 20 vol % of methyl nitrite, 20 vol % of carbon monoxide and 5 vol % of methanol was passed through, 200 ppm (by volume) of hydrogen chloride gas being added to this gas mixture. The gas flowing out of the reactor was cooled to 5° C. and the condensed phase obtained was examined by gas chromatography.

The uncondensed products were determined by IR spectroscopy and mass spectroscopy.

0.03 wt % of dimethyl oxalate, 0.1 wt % of methyl formate and 0.04 wt % of formaldehyde dimethylacetal were detected in the dimethyl carbonate obtained.

What is claimed is:

1. A process for the preparation of a dialkyl carbonate by the continuous reaction of carbon monoxide with alkyl nitrite in the gas phase on a heterogeneous catalyst, with continuous temperature control using a heat transfer medium, wherein the catalyst bed takes the form of one or more flat layers of regular shape with a thickness of 0.01–50 cm, the surface of the catalyst layers being sealed by a gas-permeable layer, and this surface, on the educt feed side and/or on the product discharge side, facing a wall of similar regular shape, at a distance of 0.1–10 cm, which separates the space for the substances to be reacted from the space for the heat transfer medium, and the substances to be reacted being introduced in such a way as to flow through the catalyst bed perpendicularly to the flat catalyst layers.

2. The process of claim 1, wherein the heterogenous catalyst is one containing one or more platinum metals.

3. The process of claim 2, wherein the platinum metal is palladium.

4. The process of claim 1, wherein the catalyst bed has a thickness of 0.02–20 cm.

5. The process of claim 4, wherein the thickness is 0.05–10 cm.

6. The process of claim 4, wherein the thickness is 0.2–2 cm.

7. The process of claim 1, wherein the distance between the catalyst bed and the wall is 0.2–8.0 cm.

8. The process of claim 7, wherein the distance is 0.3–6 cm.

9. The process of claim 8, wherein the distance is 0.4–4 cm.

10. The process of claim 1, wherein the gas-permeable layer for sealing the catalyst layers take the form of a meshwork, a perforated screen or sintered material.

11. The process of claim 1, wherein the flat catalyst bed, including its gas-permeable sealing layer, has a minimum flow resistance of 1 mbar to 10 bar.

12. The process of claim 11, wherein the minimum flow resistance is 2 mbar to 1 bar.

13. The process of claim 12, wherein the minimum flow resistance is 5–500 mbar.

14. The process of claim 1, wherein the regularly shaped, flat layers of the catalyst bed take the form of hollow cylinders, sealed on one side, with diameters of 2–200 cm, several of them being arranged in the form of large aggregates.

15. The process of claim 14, wherein the hollow cylinders have a diameter of 7–100 cm.

16. The process of claim 14, wherein of the hollow cylinders are arranged as tube bundles.

17. The process of claim 1, which is carried out at a pressure of 0.1–10 bar.

18. The process of claim 1, wherein the catalyst temperature is 50–150° C.

19. The process of claim 1, which is carried out with a volume ratio alkyl nitrite:carbon monoxide of 0.1 to 10:1.

20. The process of claim 1, wherein a palladium salt applied to a support is used as the catalyst.

* * * * *